US011089294B2

(12) United States Patent
Niwa (10) Patent No.: US 11,089,294 B2
(45) Date of Patent: Aug. 10, 2021

(54) ENDOSCOPE INSPECTION SYSTEM, ENDOSCOPE INSPECTION APPARATUS, ENDOSCOPE PACKAGE, AND ENDOSCOPE INSPECTION METHOD

(71) Applicant: OLYMPUS CORPORATION, Tokyo (JP)

(72) Inventor: Hiroshi Niwa, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/907,417

(22) Filed: Jun. 22, 2020

(65) Prior Publication Data

US 2020/0322598 A1 Oct. 8, 2020

Related U.S. Application Data

(63) Continuation of application No. PCT/JP2018/029832, filed on Aug. 8, 2018.

(30) Foreign Application Priority Data

Dec. 22, 2017 (JP) .............................. JP2017-247011

(51) Int. Cl.
*H04N 5/232* (2006.01)
*H04N 17/00* (2006.01)
(Continued)

(52) U.S. Cl.
CPC ......... *H04N 17/002* (2013.01); *A61B 1/0002* (2013.01); *A61B 1/00009* (2013.01);
(Continued)

(58) Field of Classification Search
None
See application file for complete search history.

(56) References Cited

U.S. PATENT DOCUMENTS

2007/0219410 A1* 9/2007 Onoda .................. A61B 5/062
600/117
2008/0242929 A1 10/2008 Ito
(Continued)

FOREIGN PATENT DOCUMENTS

EP 1 974 652 A1 10/2008
EP 3 145 176 A1 3/2017
(Continued)

OTHER PUBLICATIONS

International Search Report dated Oct. 9, 2018 received in International Application No. PCT/JP2018/029832, together with an English-language translation.

*Primary Examiner* — Eileen M Adams
(74) *Attorney, Agent, or Firm* — Scully, Scott, Murphy & Presser, P.C.

(57) ABSTRACT

An endoscope inspection system includes an endoscope inspection apparatus and a package that packages an endoscope. The endoscope inspection apparatus includes a communication connector and a processor. The processor drives an image pickup device circuit of the endoscope to receive a response signal, determines based on the response signal whether a status of an image pickup device circuit is good or poor, and notifies a result of determination. The package includes a first fixing shape portion that fixes the packaged endoscope connector and a first fitting shape portion fitted with the communication connector such that an endoscope-side communication terminal of the fixed endoscope connector is electrically connected to an inspection apparatus-side communication terminal of the communication connector.

11 Claims, 8 Drawing Sheets

(51) Int. Cl.
*A61B 1/00* (2006.01)
*A61B 1/06* (2006.01)
*H04N 5/225* (2006.01)

(52) U.S. Cl.
CPC ...... *A61B 1/00011* (2013.01); *A61B 1/00057* (2013.01); *A61B 1/00059* (2013.01); *A61B 1/00144* (2013.01); *A61B 1/0661* (2013.01); *H04N 5/2256* (2013.01); *H04N 5/232* (2013.01); *H04N 2005/2255* (2013.01)

(56) References Cited

U.S. PATENT DOCUMENTS

| | | | | |
|---|---|---|---|---|
| 2009/0287047 | A1* | 11/2009 | Onoda | A61B 5/06 600/109 |
| 2015/0190039 | A1* | 7/2015 | Takahashi | G02B 23/2423 600/109 |
| 2017/0086649 | A1 | 3/2017 | Mizuno | |

FOREIGN PATENT DOCUMENTS

| | | |
|---|---|---|
| JP | 10-290778 A | 11/1998 |
| JP | 2008-237395 A | 10/2008 |
| JP | 2010-51440 A | 3/2010 |
| JP | 2010-88559 A | 4/2010 |
| JP | 2012-254195 A | 12/2012 |
| JP | 2016-19679 A | 2/2016 |
| JP | 2016-123825 A | 7/2016 |
| WO | 2016/059983 A1 | 4/2016 |

* cited by examiner

FIG. 9

ENDOSCOPE INSPECTION SYSTEM, ENDOSCOPE INSPECTION APPARATUS, ENDOSCOPE PACKAGE, AND ENDOSCOPE INSPECTION METHOD

CROSS REFERENCE TO RELATED APPLICATION

This application is a continuation application of PCT/JP2018/029832 filed on Aug. 8, 2018 and claims benefit of Japanese Application No. 2017-247011 filed in Japan on Dec. 22, 2017, the entire contents of which are incorporated herein by this reference.

BACKGROUND OF THE INVENTION

1. Field of the Invention

The present invention relates to an endoscope inspection system, an endoscope inspection apparatus, an endoscope package, and an endoscope inspection method that inspect a status related to an image pickup unit of an endoscope.

2. Description of the Related Art

An endoscope system is widely used in medical fields and industrial fields, the endoscope system including an endoscope provided with an image pickup device configured to capture an image of an object inside a subject, an image processing device called a video processor configured to generate an observation image obtained by performing image pickup of the object with the endoscope, and a light source device configured to generate and emit illumination light to be irradiated from the endoscope to the object.

The endoscope in such an endoscope system adopts design and structure capable of withstanding many cases in consideration of high safety, and thus can be reused over a long period of time. On the other hand, in recent years, a so-called disposable-type endoscope has also become known.

Such a disposable-type endoscope is basically assumed to be used for only one case, and thus often has a simpler structure than a reusable type endoscope.

Japanese Patent Application Laid-Open Publication No. 2010-51440 discloses an endoscope system capable of determining a breakage status of an optical fiber constituting a light guide.

A technique disclosed in Japanese Patent Application Laid-Open Publication No. 2010-51440 described above is to determine, using light receiving means including a sensor detachably attached to an insertion-portion distal end portion of an endoscope and configured to receive illumination light guided by a light guide, the breakage status of the optical fiber based on the output from the sensor.

SUMMARY OF THE INVENTION

According to an aspect of the present invention, an endoscope inspection system includes: an endoscope inspection apparatus that inspects a status of an image pickup device circuit of an endoscope; and a package that packages a predetermined portion of the endoscope, wherein the endoscope inspection apparatus includes a communication connector configured to be capable of transmitting and receiving a predetermined signal to and from the endoscope and a processor, the processor being configured to generate a drive signal that is a signal transmitted via the communication connector and is used to drive the image pickup device circuit, receive a response signal from the image pickup device circuit configured to operate by the drive signal, the response signal being a signal received via the communication connector, determine, based on the received response signal, whether the status of the image pickup device circuit is good or poor, and notify predetermined information based on a result of determination, and the package packages an endoscope connector of the endoscope, and includes a first fixing shape portion that fixes the packaged endoscope connector and a first fitting shape portion fitted with the communication connector such that an endoscope-side communication terminal of the endoscope connector fixed to the first fixing shape portion is electrically connected to an inspection apparatus-side communication terminal of the communication connector.

An endoscope inspection apparatus according to another aspect of the present invention is an endoscope inspection apparatus that inspects a status of an image pickup device circuit of an endoscope in which a predetermined portion is packaged in a package, the endoscope inspection apparatus including: a communication connector configured to be capable of transmitting and receiving a predetermined signal to and from the endoscope and fitted into a first fitting shape portion of the package; an inspection apparatus-side communication terminal provided in the communication connector and electrically connected to an endoscope-side communication terminal of an endoscope connector of the endoscope in a state where the communication connector is fitted into the first fitting shape portion; and a processor, the processor being configured to generate a drive signal that is a signal transmitted via the communication connector and is used to drive the image pickup device circuit, receive a response signal from the image pickup device circuit configured to operate by the drive signal, the response signal being a signal received via the communication connector, determine, based on the received response signal, whether the status of the image pickup device circuit is good or poor, and notify predetermined information based on a result of determination.

An endoscope package according to further another aspect of the present invention is an endoscope package that packages a predetermined portion of an endoscope, wherein the package packages an endoscope connector of the endoscope, and includes a first fitting shape portion fitted with the communication connector such that an endoscope-side communication terminal of the endoscope connector fixed to the first fixing shape portion is electrically connected to an inspection apparatus-side communication terminal of the communication connector of an endoscope inspection apparatus that inspects a status of an image pickup device circuit of the endoscope.

An endoscope inspection method according to still further another aspect of the present invention is an endoscope inspection method of inspecting a status of an image pickup device circuit of an endoscope in which a predetermined portion is packaged in a package, the method including: fitting a communication connector provided in an endoscope inspection apparatus and configured to be capable of transmitting and receiving a predetermined signal to and from the endoscope into a first fitting shape portion of the package; electrically connecting an inspection apparatus-side communication terminal of the communication connector to an endoscope-side communication terminal of an endoscope connector of the endoscope in a state where the communication connector is fitted into the first fitting shape portion; generating a drive signal that is a signal transmitted via the communication connector and is used to drive the image pickup device circuit; receiving a response signal from the image pickup device circuit configured to operate by the drive signal, the response signal being a signal received via the communication connector; determining, based on the received response signal, whether the status of the image pickup device circuit is good or poor; and notifying predetermined information based on a result of determination.

DETAILED DESCRIPTION OF THE PREFERRED EMBODIMENTS

Embodiments of the present invention will be described below with reference to the drawings.

First Embodiment

Figure 1:
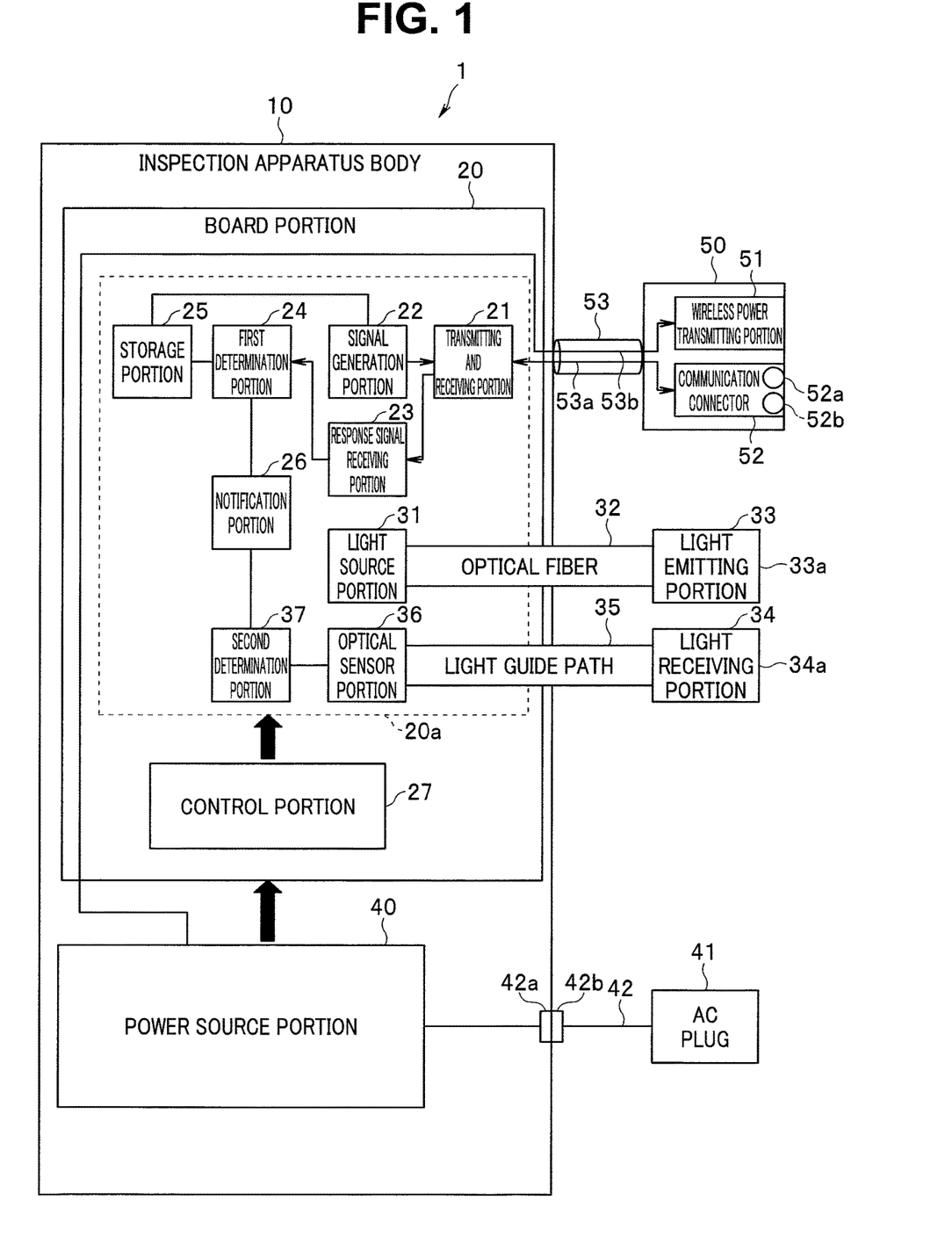
FIG. 1 is a block diagram showing an electrical configuration of an endoscope inspection apparatus of a first embodiment of the present invention.
Figure 2:
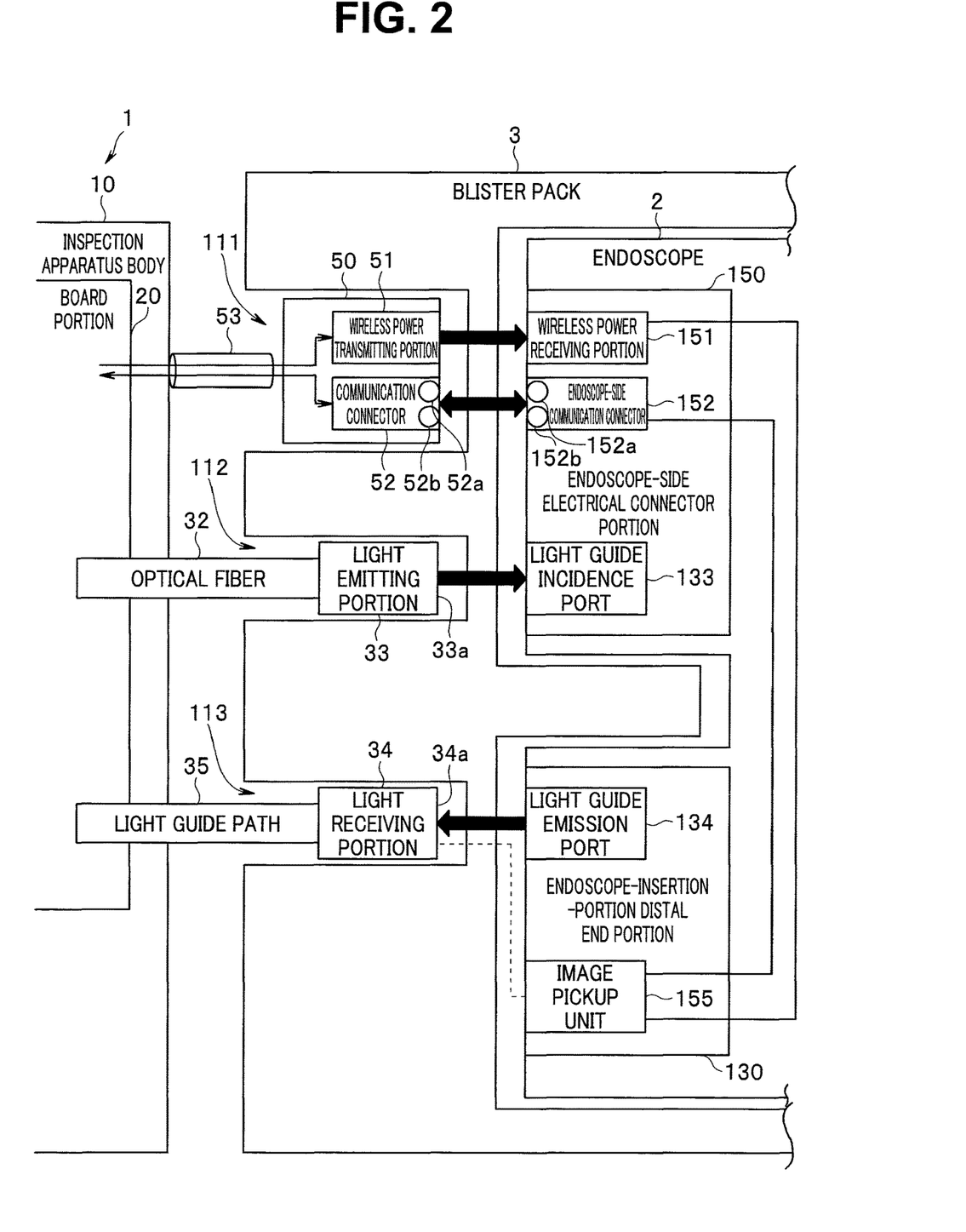
FIG. 2 is a block diagram showing an electrical connection state between the endoscope inspection apparatus of the first embodiment and an endoscope (to be inspected) packaged in a blister pack.

FIG. 1 is a block diagram showing an electrical configuration of an endoscope inspection apparatus of a first embodiment of the present invention, and FIG. 2 is a block diagram showing an electrical connection state between the endoscope inspection apparatus of the first embodiment and an endoscope to be inspected, the endoscope being packaged in a blister pack.

Figure 3:
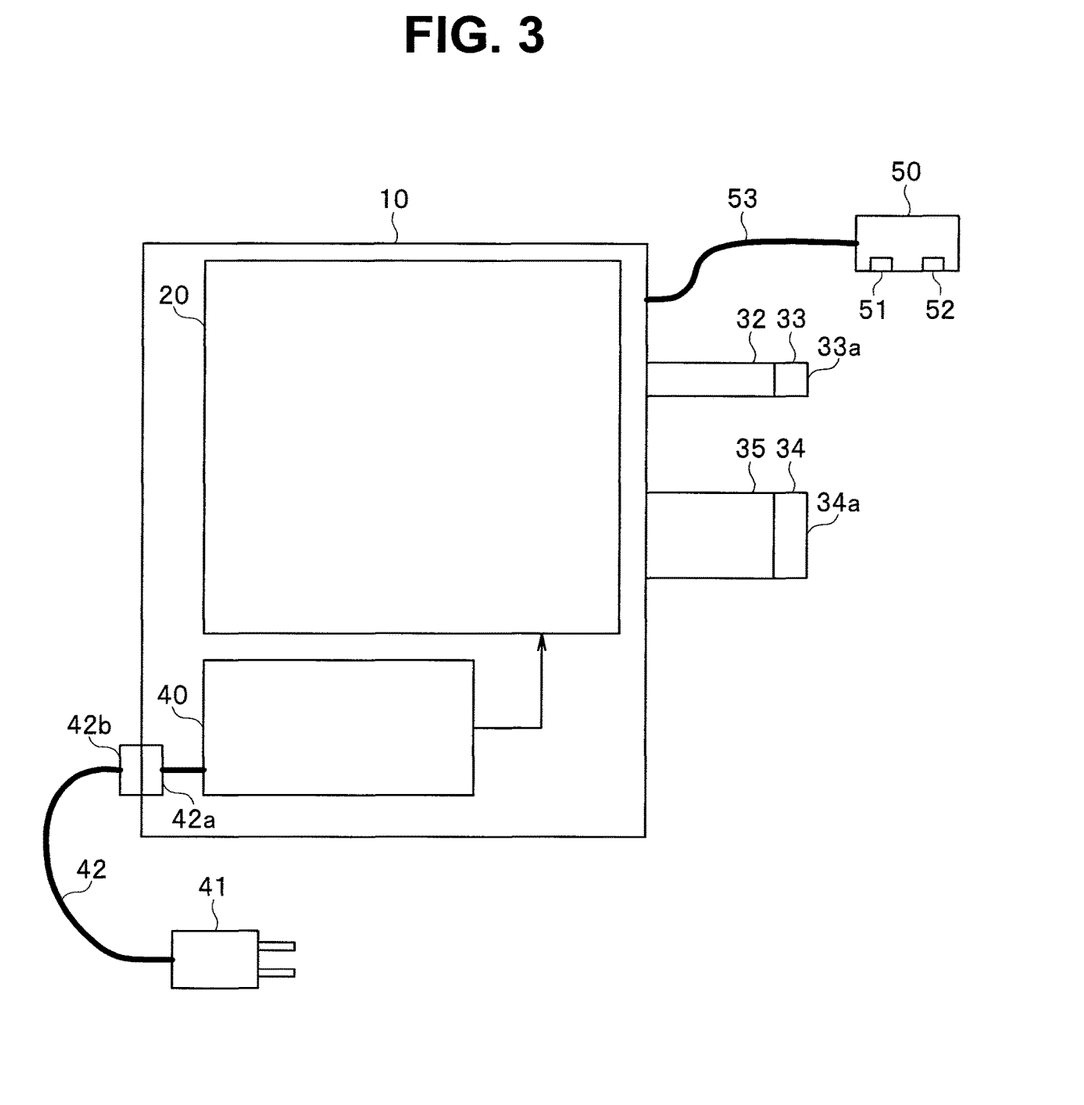
FIG. 3 is a view showing a schematic configuration of an inspection apparatus body, an electrical connector portion, a light emitting portion, and a light receiving portion in the endoscope inspection apparatus of the first embodiment.
Figure 4:
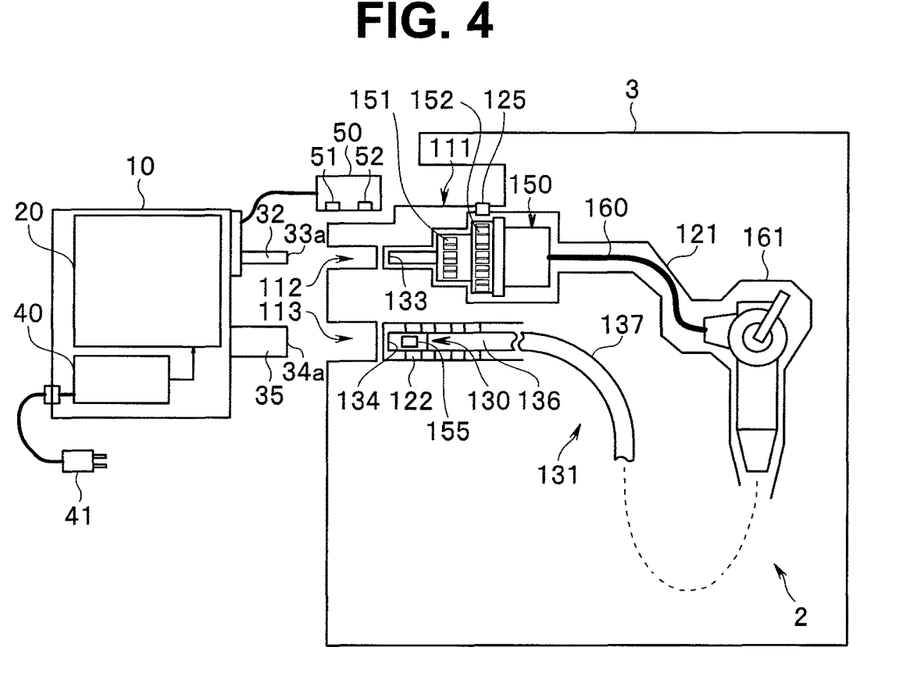
FIG. 4 is a view showing the endoscope inspection apparatus of the first embodiment and the endoscope (to be inspected) packaged in the blister pack.

In addition, FIG. 3 is a view showing a schematic configuration of an inspection apparatus body, an electrical connector portion, a light emitting portion, and a light receiving portion in the endoscope inspection apparatus of the first embodiment, and FIG. 4 is a view showing the endoscope inspection apparatus of the first embodiment and the endoscope (to be inspected) packaged in the blister pack.

<Schematic Configuration of Endoscope 2>

First, a configuration of the endoscope 2 to be inspected by the endoscope inspection apparatus will be schematically described with reference to FIGS. 2 and 4 before a description of the endoscope inspection apparatus of the first embodiment.

The endoscope 2 includes an elongated insertion portion 131 to be inserted into a body cavity and the like of a subject, an endoscope operation portion 161 disposed on a proximal end side of the insertion portion 131 to be grasped and operated by a surgeon, a universal cord 160 including one end portion provided so as to extend from a side portion of the endoscope operation portion 161, and an endoscope-side electrical connector portion 150 disposed at a proximal end side of the universal cord 160 and detachably connected to a front surface of a light source device or a video processor which are not shown.

The insertion portion 131 includes not only a rigid insertion-portion distal end portion 130 provided at the distal end side, but also a bendable bending portion 136 provided at a rear end of the insertion-portion distal end portion 130 and a flexible tube portion 137 provided at a rear end of the bending portion 136 and having a long length and flexibility.

In the present embodiment, the endoscope insertion-portion distal end portion 130 is provided with an objective optical system (not shown) including a lens into which an object image enters and an image pickup unit 155 (image pickup device circuit) including an image pickup device disposed on an image forming plane of the objective optical system.

The endoscope inspection apparatus according to the first embodiment relates to an inspection apparatus that can easily inspect a malfunction status related to the "image pickup unit" of the endoscope 2. However, in the following description of the embodiments of the present invention, the "malfunction status relating to the image pickup unit" includes not only a "malfunction status relating to the image pickup device" but also a malfunction status relating to a circuit part that drives the image pickup device or a circuit part including an electrical wiring extending to the image pickup device.

In addition, a light guide emission port 134 is formed on a distal end surface of the endoscope insertion-portion distal end portion 130 to configure an illumination portion that irradiates the object with illumination light.

The endoscope-side electrical connector portion 150 is disposed at a proximal end side of the universal cord 160. In the present embodiment, the endoscope-side electrical connector portion 150 adopts a connector, which is integrally configured by a light guide and an electrical contact, and is detachably connected to the front surface of the light source device or the video processor which are not shown.

In the first embodiment, the endoscope-side electrical connector portion 150 adopts the connector, which is integrally configured by a light guide and an electrical contact, as described above, but the endoscope-side electrical connector portion 150 is not limited to the above-described configuration and may adopt another type of connector such as a connector type in which a so-called light guide connector and a video connector are bifurcated.

Specifically, the endoscope-side electrical connector portion 150 of the present embodiment includes a pipe sleeve (not shown) projecting from the distal end of the endoscope-side electrical connector portion 150 and serving as a connection end portion of a fluid conduit and a light guide incidence port 133 that is a light guide pipe sleeve serving as a supply end portion of the illumination light.

In the first embodiment, the endoscope-side electrical connector portion 150 is formed with a wireless power receiving portion 151 and an endoscope-side communication connector 152.

In the first embodiment, the endoscope-side electrical connector portion 150 is formed with the wireless power receiving portion 151 and the endoscope-side communication connector 152 as described above, but power source supply means and communication means for a predetermined signal may be configured by other types, and, for example, the power source supply means and the communication means for the predetermined signal may be configured by one kind of connector mechanism.

The wireless power receiving portion 151 serves as a power source supply port configured to operate the endoscope 2 in cooperation with a wireless power transmitting portion disposed in the video processor when the endoscope 2 is connected to the video processor.

In the present embodiment, when the endoscope 2 is inspected, the wireless power receiving portion 151 serves as a supply port that receives a power source supplied from the inspection apparatus body 10. For example, a predetermined power source voltage supplied to the wireless power receiving portion 151 is also supplied to the image pickup unit 155 through a known power source line.

Similarly, the endoscope-side communication connector 152 serves as communication means that transmits and receives a predetermined signal to/from the endoscope 2 when the endoscope 2 is connected to the video processor.

In the present embodiment, when the endoscope 2 is inspected, the endoscope-side communication connector 152 serves as a receiving portion configured to receive a predetermined signal from the inspection apparatus body 10 and also serves as a transmitting portion of a response signal indicating a status related to the image pickup unit 155.

<Configuration of Endoscope Inspection Apparatus>

The endoscope inspection apparatus of the first embodiment will be described below.

FIG. 1 is a block diagram showing an electrical configuration of the endoscope inspection apparatus of the first embodiment of the present invention, and FIG. 2 is a block diagram showing an electrical connection state between the endoscope inspection apparatus of the first embodiment and the endoscope (to be inspected) packaged in the blister pack. In addition, FIG. 3 is a view showing a schematic configuration of the inspection apparatus body, the electrical connector portion, the light emitting portion, and the light receiving portion in the endoscope inspection apparatus of the first embodiment.

As shown in FIGS. 1 and 3, the endoscope inspection apparatus of the first embodiment includes an inspection apparatus body 10, an apparatus-side electrical connector portion 50 extending from the inspection apparatus body 10, an electrical cable 53, an optical fiber 32, a light emitting portion 33 (a light emitting component), a light receiving portion 34 (a light receiving component), a light guide path 35, and an AC plug 41 configured to supply a power source to the inspection apparatus body 10, for example.

In the first embodiment, the inspection apparatus body 10 is configured to receive the supply of the power source, which is a commercial power source, via the AC plug 41, but may be configured to receive the supply of a predetermined power source from a predetermined battery mounted on the inspection apparatus body 10 without being limited to such a configuration.

The inspection apparatus body 10 includes a board portion 20 on which various circuit portions related to the endoscope inspection are arranged and a power source portion 40 configured to generate a power source to be supplied to each of the circuits in the board portion 20 and the endoscope 2 to be inspected.

<Schematic Configuration of Power Source Portion 40 in Inspection Apparatus Body 10>

The inspection apparatus body 10 includes the power source portion 40 configured to supply the power source to each of the circuits in the board portion 20 and the image pickup unit 155 in the endoscope 2 to be inspected.

An AC power cord 42 is connected to the power source portion 40, and the AC plug 41 is provided at a distal end portion of the AC power cord 42 to receive the supply of a primary power source from the commercial power source. In the present embodiment, the AC power cord 42 is configured to be detachable from connection connectors 42a and 42b disposed in the inspection apparatus body 10.

On the other hand, the power source portion 40 generates a predetermined DC power source voltage to be supplied to each of the circuits in the board portion 20 and a predetermined DC power source voltage to be supplied to the image pickup unit 155 in the endoscope 2 to be inspected, and outputs such voltages to each of the circuits. Note that a DC power source output directed to the endoscope 2 is configured to be connected to a power source line 53b in an electrical cable 53, which will be described below, through the inside of the board portion 20.

<Schematic Configuration of Board Portion 20 in Inspection Apparatus Body 10>

As shown in FIG. 1, for example, the board portion 20 includes function portions having respective functions, that is, mainly includes a transmitting and receiving portion 21 capable of transmitting and receiving a predetermined signal to/from the endoscope 2 to be inspected, a signal generation portion 22 configured to generate a drive signal to be transmitted to the endoscope 2, a response signal receiving portion 23 capable of receiving a response signal from the endoscope 2, a first determination portion 24 configured to determine whether a status of the image pickup unit 155 in the endoscope 2 is good or poor, a storage portion 25 (memory) configured to store information related to the drive signal, and a notification portion 26 configured to notify predetermined information based on the result determined by the first determination portion 24.

Each of the function portions, for example, the first determination portion 24 mainly serves to inspect the image pickup unit 155 in the endoscope 2 to be inspected.

In addition, the board portion 20 includes a light source portion 31 (light source) configured to generate inspection light to be supplied to the endoscope 2, an optical fiber 32 configured to transmit the inspection light, a light guide path 35 configured to transmit the inspection light sent from the endoscope 2, an optical sensor portion 36 (optical sensor) configured to convert the inspection light into a predetermined electrical signal and output the electrical signal, and a second determination portion 37 configured to determine whether a status related to the light guide in the endoscope 2 is good or poor.

Each of the function portions, such as the second determination portion 37 mainly serves to inspect the illumination optical system in the endoscope 2 to be inspected.

Further, the board portion 20 includes a control portion 27 configured to control the respective function portions (portions indicated by reference numeral 20a in FIG. 1) described above. The control portion 27 controls operations of respective circuits in the respective function portions 20a according to operation (not shown). Note that the signal generation portion 22, the response signal receiving portion 23, the first determination portion 24, the notification portion 26, the control portion 27, and the second determination portion 37 are configured to perform respective functions by causing a processor including a CPU to execute software. However, the respective portions may be configured by electronic circuits, respectively, without being limited to such a configuration, and may be configured by a processor including an integrated circuit such as an FPGA (field programmable gate array) including circuit portions corresponding to the respective portions.

<Detailed Configuration of Board Portion 20>

A detailed configuration of the above-described respective function portions in the board portion 20 will be described in detail below together with the apparatus-side electrical connector portion 50, the light emitting portion 33, and the light receiving portion 34 which extend from the inspection apparatus body 10.

As described above, the board portion 20 includes, as image-pickup-unit inspection function portions that inspect the image pickup unit 155 in the endoscope 2 to be inspected, the transmitting and receiving portion 21, the signal generation portion 22, the response signal receiving portion 23, the first determination portion 24, the storage portion 25, and the notification portion 26.

The storage portion 25 stores information related to the drive signal corresponding to the type of endoscope to be inspected. The drive signal is a signal used to drive the image pickup unit 155 in the endoscope 2 when the endoscope 2 is connected to the inspection apparatus body 10 in a state of being housed in the blister pack 3.

On the other hand, the storage portion 25 is configured to further store pattern information of a reference response signal corresponding to the type of endoscope (such a configuration will be described below).

The signal generation portion 22 is connected to the storage portion 25 and the transmitting and receiving portion 21, and is configured to generate a drive signal corresponding to the type of the endoscope 2 (to be inspected) connected to the inspection apparatus body 10, based on the information stored in the storage portion 25 under the control of the control portion 27 and output the drive signal to the transmitting and receiving portion 21 in the subsequent stage.

The drive signal generated by the signal generation portion 22 is transmitted to the endoscope 2, under the control of the control portion 27, through the transmitting and receiving portion 21, the apparatus-side communication connector 52, and an endoscope-side communication connector 152 (to be described below).

The transmitting and receiving portion 21 is connected to the signal generation portion 22 and the response signal receiving portion 23, and has a function of transmitting the drive signal generated by the signal generation portion 22 to the endoscope 2 and receiving the response signal from the endoscope 2, under the control of the control portion 27.

Here, the transmitting and receiving portion 21 is a part of the communication portions capable of transmitting and receiving a predetermined signal to/from the endoscope 2 to be inspected. The predetermined signal corresponds to the drive signal and a response signal to be described below. Regarding the communication portions, the apparatus-side communication connector 52 in the apparatus-side electrical connector portion 50 is also a part of the communication portions.

In addition, a communication line 53a extends from the transmitting and receiving portion 21, and the communication line 53a is connected to the apparatus-side communication connector 52 in the apparatus-side electrical connector portion 50 to be described below. On the other hand, an electrical cable 53 extends from the inspection apparatus body 10, and the communication line 53a is provided inside the electrical cable 53 together with the power source line 53b.

Then, the transmitting and receiving portion 21 transmits, under the control of the control portion 27, the drive signal generated by the signal generation portion 22 to the endoscope 2 through the communication line 53a, the apparatus-side communication connector 52, and the endoscope-side communication connector 152 when the apparatus-side electrical connector portion 50 provided with the apparatus-side communication connector 52 is electrically connected to the endoscope 2.

As described above, during the inspection of the endoscope, the drive signal generated by the signal generation portion 22 is inputted to the endoscope 2 connected to the inspection apparatus body 10 to drive the image pickup unit 155. On the other hand, the endoscope 2 outputs the response signal corresponding to the operation of the image pickup unit 155 driven by the drive signal.

As described above, the response signal receiving portion 23 can receive the response signal from the endoscope 2 under the control of the control portion 27, through the communication portions (for example, the endoscope-side communication connector 152, the apparatus-side communication connector 52, the communication line 53a, and the transmitting and receiving portion 21).

In other words, according to the present embodiment, during the inspection of the endoscope 2, the response signal receiving portion 23 is configured to receive the response signal outputted from the endoscope 2, under the control of the control portion 27, through the apparatus-side communication connector 52, the communication line 53a, and the transmitting and receiving portion 21 which are described above, and outputs the response signal to the first determination portion 24 in the subsequent stage.

Under the control of the control portion 27, the first determination portion 24 determines, based on the response signal received by the response signal receiving portion 23, whether the status of the image pickup unit 155 in the endoscope is good or poor. For example, the first determination portion 24 determines whether the status of the image pickup unit 155 is good or poor, based on "color chart information", "white flaw information", "noise information", and "information on presence or absence of malfunction of the image pickup device itself" obtained from the response signal related to the image information acquired by the image pickup unit 155 of the endoscope 2.

In the present embodiment, the response signal is inspected with reference to the "pattern information of the reference response signal" stored in the storage portion 25 at the time of the determination of the status.

On the other hand, the notification portion 26 notifies the status by predetermined warning information, for example, a warning sound, a warning message, or flashing of the display portion when there is any trouble in the image pickup unit 155 based on the result determined by the first determination portion 24.

<Configuration of Electrical Cable 53>

As described above, the electrical cable 53 extends from the inspection apparatus body 10 (see FIGS. 1 and 3). Further, the electrical cable 53 includes the communication line 53a and the power source line 53b provided therein, as shown in FIG. 1.

The communication line 53a has one end connected to the transmitting and receiving portion 21 and the other end connected to the apparatus-side communication connector 52 in the apparatus-side electrical connector portion 50. In addition, the power source line 53b has one end connected to the output portion of the power source portion 40 via the board portion 20 and the other end connected to the wireless power transmitting portion 51 in the apparatus-side electrical connector portion 50.

<Configuration of Apparatus-Side Electrical Connector Portion 50>

As shown in FIGS. 1 and 2, the apparatus-side electrical connector portion 50 is disposed at the distal end portion of the electrical cable 53 extending from the inspection apparatus body 10, and is fitted into a first fitting portion 111 in the blister pack 3 (to be described in detail below) configured to package the endoscope 2 to be inspected (the first fitting portion 111 will be described in detail below).

In addition, the apparatus-side electrical connector portion 50 is internally provided with the wireless power transmitting portion 51 configured to supply a power source to the endoscope 2 and the apparatus-side communication connector 52 configured to transmit and receive a predetermined signal to/from the endoscope 2.

The wireless power transmitting portion 51 includes a wireless power transmitting coil and a coil drive portion. The coil drive portion converts the DC power source voltage outputted from the power source portion 40 via the power source line 53b provided inside the electrical cable 53 into a predetermined alternating voltage and applies the alternating voltage to the wireless power transmitting coil, and thus the wireless power transmitting coil is configured to transmit predetermined power source energy.

In other words, the wireless power transmitting portion 51 is disposed to face the wireless power receiving portion 151 and supplies predetermined electrical energy to the wireless power receiving portion 151 by known electromagnetic induction when the apparatus-side electrical connector portion 50 is fitted and arranged in the first fitting portion 111 of the blister pack 3 during the inspection of the image pickup unit of the endoscope 2.

On the other hand, the apparatus-side communication connector 52 includes apparatus-side communication connector terminals 52a and 52b connected to the communication line 53a provided inside the electrical cable 53. The apparatus-side communication connector terminals 52a and 52b are formed such that terminal portions are exposed in the present embodiment.

The apparatus-side communication connector terminals 52a and 52b are electrically connected to endoscope-side communication connector terminals 152a and 152b provided inside the endoscope-side communication connector 152 via an exposed conduction portion 125 (see FIGS. 4 and 5) formed in the blister pack 3 when the apparatus-side electrical connector portion 50 is fitted and arranged in the first fitting portion 111 of the blister pack 3 during the inspection of the image pickup unit of the endoscope 2.

In other words, as described above, the exposed conduction portion 125 (see FIG. 4) is formed in the blister pack 3 such that the endoscope-side communication connector terminals 152a and 152b are electrically conducted with the outside of the blister pack 3 under maintenance of a clean state of the endoscope 2 housed in the blister pack.

Figure 5:
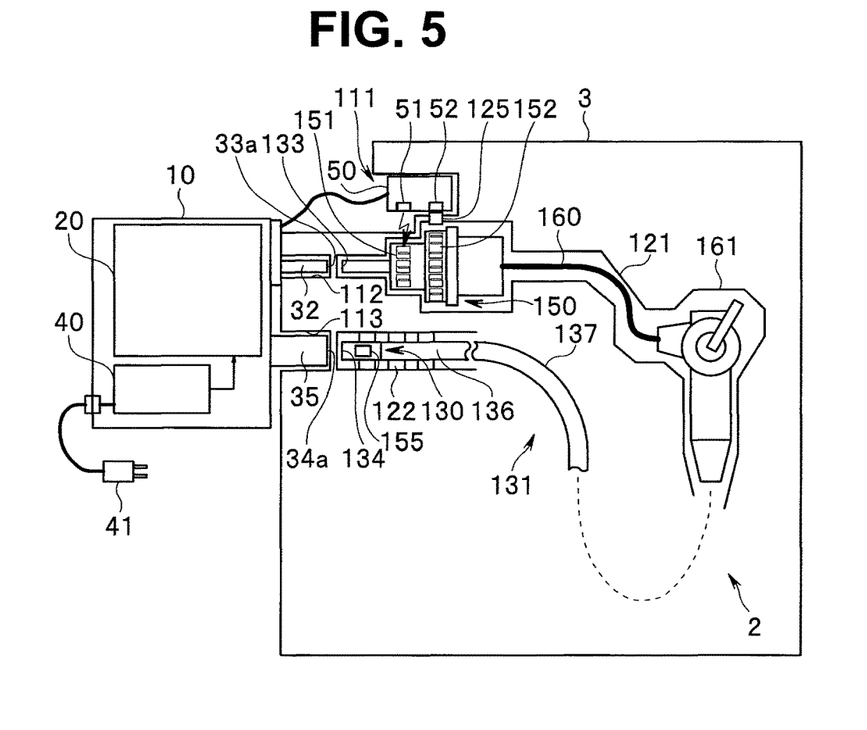
FIG. 5 is a view showing a state where the endoscope inspection apparatus of the first embodiment is connected to the endoscope (to be inspected) packaged in the blister pack.

On the other hand, the exposed conduction portion 125 is also electrically connected to the apparatus-side communication connector 52 of the apparatus-side electrical connector portion 50 when the apparatus-side electrical connector portion 50 is fitted and arranged in the first fitting portion 111 (see FIG. 5). Thus, the apparatus-side communication connector terminals 52a and 52b are electrically connected to the endoscope-side communication connector terminals 152a and 152b, respectively.

<Illumination-Optical-System Inspecting Portion in Board Portion 20>

The board portion 20 includes, in addition to the image-pickup-unit inspection function portions described above, the light source portion 31, the optical fiber 32, the light guide path 35, the optical sensor portion 36, the second determination portion 37, and the notification portion 26, as function portions that inspect the illumination optical system of the endoscope 2 to be inspected. The respective function portions will be described below together with the light emitting portion 33 and the light receiving portion 34.

The light source portion 31 generates inspection light to be used for inspecting the illumination optical system in the endoscope 2. The inspection light is set to light sufficient to inspect the endoscope 2 in the present embodiment.

In addition, the optical fiber 32 is connected to the output end of the light source portion 31 and is provided so as to extend from the inspection apparatus body 10 to transmit the inspection light generated by the light source portion 31. Further, the light emitting portion 33 is provided at a distal end of the optical fiber 32.

The light emitting portion 33 is provided at the distal end of the optical fiber 32 extending from the inspection apparatus body 10 and is fitted into a second fitting portion 112 of the blister pack 3 (the second fitting portion 112 will be described in detail below). The blister pack 3 functions as a package that packages a predetermined portion of the endoscope 2, and will be described in detail below.

Further, a light emitting port 33a is formed on a distal end surface of the light emitting portion 33, and emits the inspection light transmitted from the light source portion 31 via the optical fiber 32 to the light guide incidence port 133 of the endoscope 2 housed in the blister pack 3.

The light receiving portion 34 is provided at a distal end portion of the light guide path 35 extending from the inspection apparatus body 10, and is fitted into a third fitting portion 113 of the blister pack 3 (the third fitting portion 113 will be described in detail below).

A light receiving surface 34a is formed on a distal end surface of the light receiving portion 34, and receives the inspection response light emitted from the light guide emission port 134 of the endoscope 2 housed in the blister pack 3.

The light guide path 35 is provided so as to extend from the inspection apparatus body 10, and has one end at which the light receiving portion 34 is formed and the other end connected to the optical sensor portion 36. Then, the light guide path 35 transmits the inspection response light, which is received to the light receiving surface 34a of the light receiving portion 34 from the endoscope 2, to the optical sensor portion 36.

In addition, the optical sensor portion 36 in the illumination-optical-system inspection function portion on the board portion 20 receives the inspection response light transmitted from the endoscope 2 through the light guide path 35, and converts the light into a predetermined electrical signal and outputs the signal.

Furthermore, the second determination portion 37 receives the electrical signal from the optical sensor portion 36, and determines based on the electrical signal whether the status of the illumination optical system such as the light guide in the endoscope 2 to be inspected is good or poor.

The notification portion 26 has a function of notifying predetermined information based on the result determined by the first determination portion 24 and also notifying predetermined information based on the result determined by the second determination portion 37.

<Configuration of Blister Pack 3>

As described above, the endoscope inspection apparatus of the present embodiment is to inspect the endoscope 2, and particularly to determine whether the status of the image pickup unit is good or poor, but the endoscope 2 is inspected in a state of being packaged in the blister pack 3.

As shown in FIGS. 2 and 4, the blister pack 3 configured to package the endoscope 2 applied to the endoscope inspection apparatus of the present embodiment is a package that packages predetermined portions of the endoscope 2, for example, the endoscope-side electrical connector portion 150, the universal cord 160, the endoscope operation portion 161, and the endoscope insertion portion 131 (including the endoscope insertion-portion distal end portion 130, the bending portion 136, and the flexible tube portion 137).

In other words, the blister pack 3 applied to the present embodiment is a package dedicated for the endoscope 2 in which a packaging portion is formed according to the size and shape of each of the predetermined portions in the predetermined endoscope 2.

On the other hand, as shown in FIG. 4, the blister pack 3 is formed with a first fixing portion 121 (first fixing shape portion) configured to correctly fix the endoscope-side electrical connector portion 150 of the packaged endoscope 2 and a second fixing portion 122 (second fixing shape portion) configured to fix the endoscope insertion-portion distal end portion 130 and the bending portion 136.

In addition, the blister pack 3 includes the first fitting portion 111 (first fitting shape portion) configured to fit the apparatus-side electrical connector portion 50 such that the wireless power receiving portion 151 of the endoscope-side electrical connector portion 150 fixed by the first fixing portion 121 is disposed to rightly face the wireless power transmitting portion 51 of the apparatus-side electrical connector portion 50 and the endoscope-side communication connector terminals 152a and 152b of the endoscope-side electrical connector portion 150 are reliably electrically connected to the apparatus-side communication connector terminals 52a and 52b of the apparatus-side electrical connector portion 50 via the exposed conduction portion 125.

Further, the blister pack 3 includes a second fitting portion 112 (second fitting shape portion) configured to fit the light emitting portion 33 such that the inspection light emitted from the light emitting portion 33 is incident on the light guide incidence port 133 of the endoscope-side electrical connector portion 150 fixed by the first fixing portion 121.

Further, the blister pack 3 includes a third fitting portion 113 (third fitting shape portion) configured to fit the light receiving portion 34 such that the light receiving surface 34a of the light receiving portion 34 can reliably receive the inspection response light emitted from the light guide emission port 134 of the endoscope insertion-portion distal end portion 130 fixed by the second fixing portion 122.

<Inspection of Endoscope Using Endoscope Inspection Apparatus>

A mode will be described in which the endoscope 2 packaged in the blister pack 3 is inspected using the endoscope inspection apparatus of the present embodiment having the above-described configuration.

FIG. 2 is a block diagram showing the electrical connection state between the endoscope inspection apparatus of the first embodiment and the endoscope (to be inspected) packaged in the blister pack. In addition, FIG. 4 is a view showing the endoscope inspection apparatus of the first embodiment and the endoscope (to be inspected) packaged in the blister pack, and FIG. 5 is a view showing a state where the endoscope inspection apparatus of the first embodiment is connected to the endoscope (to be inspected) packaged in the blister pack.

As shown in FIGS. 2, 4, and 5 described above, when the endoscope 2 packaged in the blister pack 3 is inspected, the apparatus-side electrical connector portion 50, the optical fiber 32 (including the light emitting portion 33 and the light emitting port 33a), and the light guide path 35 (including the light receiving portion 34 and the light receiving surface 34a) extending from the inspection apparatus body 10 are respectively connected to the first fitting portion 111, the second fitting portion 112, and the third fitting portion 113, which are formed in the blister pack 3, in a fitting manner.

When the apparatus-side electrical connector portion 50 is fitted into the first fitting portion 111, the wireless power transmitting portion 51 and the apparatus-side communication connector 52 provided inside the apparatus-side electrical connector portion 50 come close to the wireless power receiving portion 151 and the endoscope-side communication connector 152 of the endoscope-side electrical connector portion 150, respectively.

In the wireless power transmitting portion 51 close to the wireless power receiving portion 151, the inscribed coil drive portion converts the DC power source voltage sent from the power source portion 40 via the power source line 53b into a predetermined alternating voltage, and applies the alternating voltage to the wireless power transmitting coil. The wireless power transmitting coil transmits predetermined power source energy to the wireless power receiving portion 151.

In other words, the wireless power transmitting portion 51 is disposed to face the wireless power receiving portion 151 and supplies predetermined electrical energy to the wireless power receiving portion 151 by known electromagnetic induction when the apparatus-side electrical connector portion 50 is fitted and arranged in the first fitting portion 111 of the blister pack 3 during the inspection of the image pickup unit of the endoscope 2.

On the other hand, the apparatus-side communication connector terminals 52a and 52b of the apparatus-side communication connector 52 connected to the communication line 53a provided inside the electrical cable 53 are electrically connected to the endoscope-side communication connector terminals 152a and 152b provided in the endoscope-side communication connector 152, respectively, via the exposed conduction portion 125 (see FIGS. 4 and 5) formed in the blister pack 3.

Further, when the light emitting portion 33 formed at the distal end portion of the optical fiber 32 is fitted into the second fitting portion 112, the light emitting port 33a is disposed to face the light guide incidence port 133 in the endoscope-side electrical connector portion 150.

Further, the light receiving portion 34 formed at the distal end portion of the light guide path 35 is disposed such that the light receiving surface 34a faces the light guide emission port 134.

As described above, after the apparatus-side electrical connector portion 50, the light emitting portion 33, and the light receiving portion 34 are fitted into the first fitting portion 111, the second fitting portion 112, and the third fitting portion 113 of the blister pack 3, respectively, the power source is supplied from the power source portion 40 of the inspection apparatus body 10 to the respective circuit of the board portion 20 by operation means (not shown), and the power source is supplied to the respective circuits including the image pickup unit 155 in the endoscope 2 via the power source line 53b, the wireless power transmitting portion 51, and the wireless power receiving portion 151 of the electrical cable 53 at the same time.

On the other hand, the signal generation portion 22 of the inspection apparatus body 10 generates, under the control of the control portion 27, the drive signal corresponding to the type of the endoscope 2 based on the information stored in the storage portion 25 and outputs the drive signal. The drive signal is outputted from the transmitting and receiving portion 21 and is transmitted from the endoscope-side communication connector 152 connected to the apparatus-side communication connector 52 to the image pickup unit 155 via the communication line 53a.

The endoscope 2 sends the response signal corresponding to the operation of the image pickup unit 155 driven by the drive signal toward the inspection apparatus body 10.

Then, the response signal receiving portion 23 in the inspection apparatus body 10 receives, under the control of the control portion 27, the response signal from the endoscope 2 via the communication portions (including the endoscope-side communication connector 152, the apparatus-side communication connector 52, the communication line 53a, and the transmitting and receiving portion 21) as described above.

Subsequently, the response signal receiving portion 23 outputs the response signal received via the transmitting and receiving portion 21 to the first determination portion 24 in the subsequent stage.

As described above, under the control of the control portion 27, the first determination portion 24 determines, based on the response signal received by the response signal receiving portion 23, whether the status of the image pickup unit 155 in the endoscope is good or poor. For example, the first determination portion 24 determines whether the status of the image pickup unit 155 is good or poor, based on "color chart information", "white flaw information", "noise information", and "information on presence or absence of malfunction of the image pickup device itself" obtained from the response signal related to the image information acquired by the image pickup unit 155 of the endoscope 2.

In the present embodiment, as described above, the response signal is inspected with reference to the "pattern information of the reference response signal" stored in the storage portion 25 at the time of the determination of the status.

On the other hand, the notification portion 26 notifies the status by predetermined warning information, for example, a warning sound, a warning message, or flashing of the display portion when there is any trouble in the image pickup unit 155 based on the result determined by the first determination portion 24.

As described above, according to the endoscope inspection apparatus of the first embodiment, it is possible to easily inspect the malfunction status of the image pickup unit in the endoscope.

<First Modification>

A first modification of the first embodiment of the present invention will be described below.

An endoscope inspection apparatus of the first modification has a main configuration similar to the configuration of the first embodiment, and a blister pack 3A is also similar to the blister pack of the first embodiment except that the shape of the first fitting portion fitted with the apparatus-side electrical connector portion of the inspection apparatus body 10 is different. Therefore, only the differences from the first embodiment will be described below, and the description of the common components will not be presented.

Figure 6:
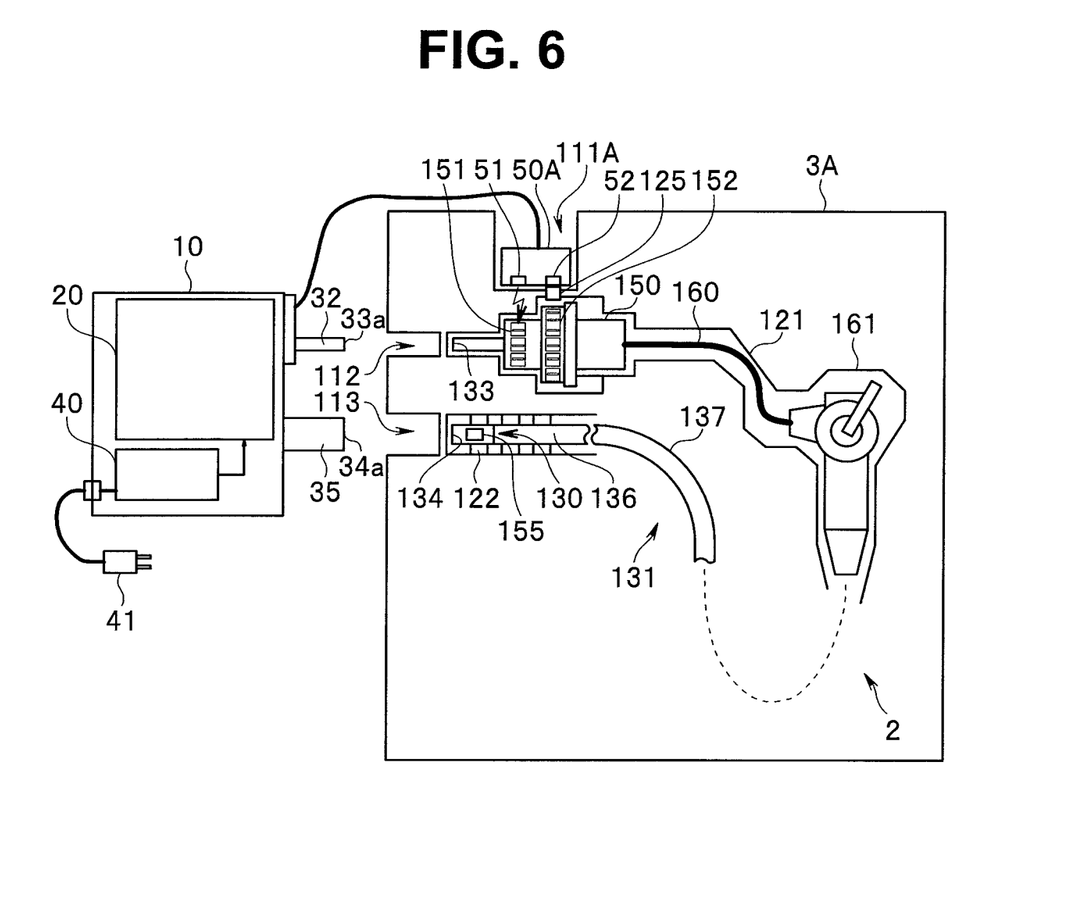
FIG. 6 is a view showing a state where an endoscope inspection apparatus of a first modification of the present invention is connected to an endoscope (to be inspected) packaged in a blister pack.

FIG. 6 is a view showing a state in which an endoscope inspection apparatus of the first modification of the present invention is connected to an endoscope (to be inspected) packaged in a blister pack.

As shown in FIG. 6, the blister pack 3A corresponding to the endoscope inspection apparatus of the first modification is formed with a first fitting portion 111A having a different shape from the first fitting portion 111 of the blister pack 3 described above. In other words, a first fitting portion 111A is formed such that an apparatus-side electrical connector portion 50A extending from the inspection apparatus body 10 can be inserted from above the paper surface of FIG. 6.

Other configurations, functions, and effects are similar to the configurations, the functions, and the effects of the first embodiment, and will not be described in detail.

Second Embodiment

A second embodiment of the present invention will be described below.

Figure 7:
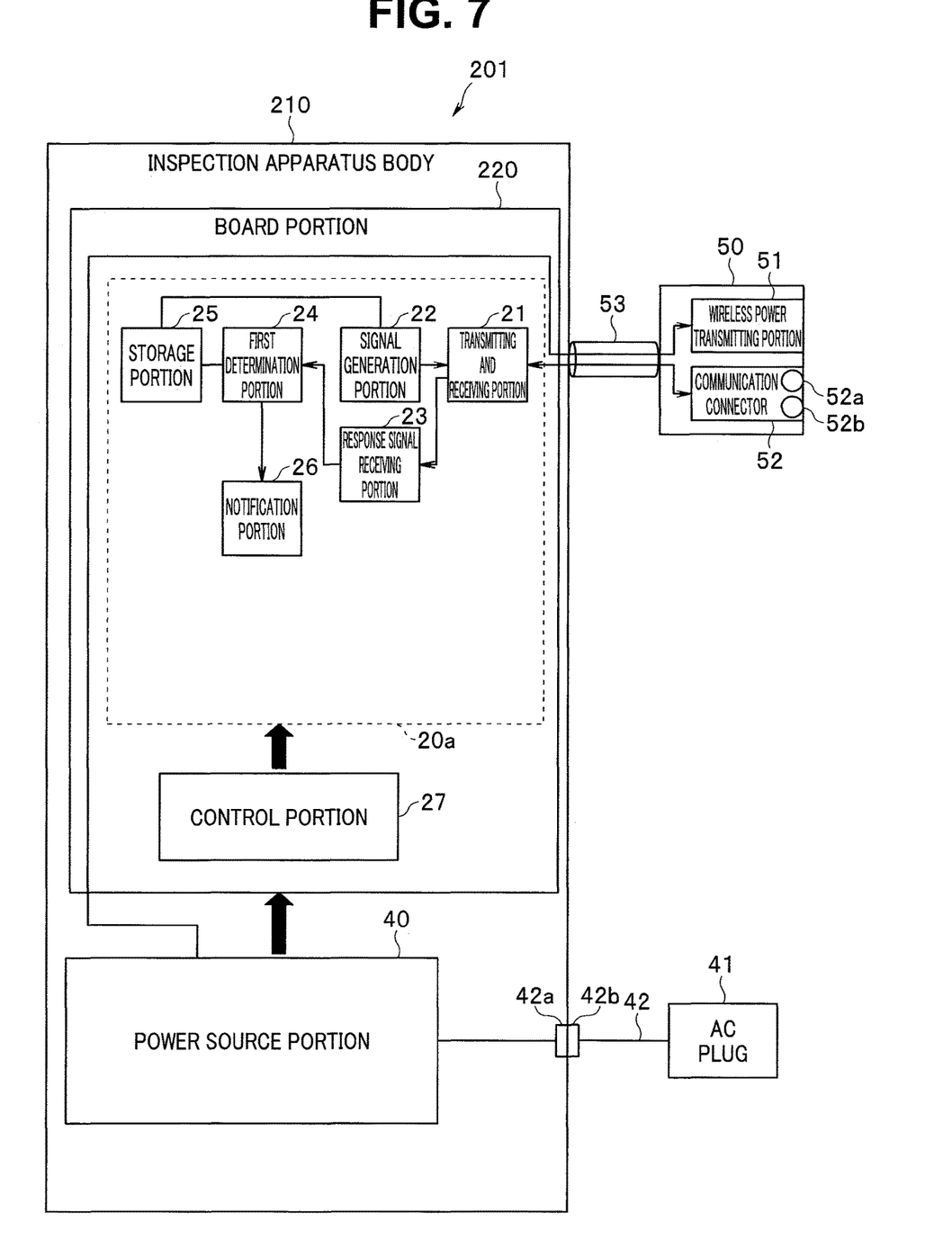
FIG. 7 is a block diagram showing an electrical configuration of an endoscope inspection apparatus of a second embodiment of the present invention.

FIG. 7 is a block diagram showing an electrical configuration of an endoscope inspection apparatus of a second embodiment of the present invention.

An endoscope inspection apparatus 201 of the second embodiment has a configuration in which the illumination-optical-system inspection portion is omitted in the inspection apparatus body 10 of the first embodiment and the inspection portion of the image pickup unit is specialized. Therefore, only the differences from the first embodiment will be described below, and the description of the common components will not be presented.

As shown in FIG. 7, the endoscope inspection apparatus of the second embodiment includes an inspection apparatus body 210, an apparatus-side electrical connector portion 50 provided to extend from the inspection apparatus body 210, an electrical cable 53, and an AC plug 41 configured to supply a power source to the inspection apparatus body 210.

On the other hand, the endoscope inspection apparatus of the second embodiment does not include the optical fiber 32, the light emitting portion 33, the light receiving portion 34, and the light guide path 35 provided in the endoscope inspection apparatus of the first embodiment.

In addition, a board portion 220 in the inspection apparatus body 210 of the second embodiment includes, as image-pickup-unit inspection function portions that inspect an image pickup unit 155 of the endoscope 2 to be inspected, a transmitting and receiving portion 21, a signal generation portion 22, a response signal receiving portion 23, a first determination portion 24, a storage portion 25, and a notification portion 26 as in the first embodiment, but does not include the circuit portions related to the illumination-optical-system inspection portion.

The endoscope inspection apparatus of the second embodiment cannot perform the inspection regarding the illumination optical system in the endoscope 2 as compared with the first embodiment, but has the inspection function of inspecting the image pickup unit of the endoscope 2 as in the first embodiment.

As described above, the endoscope inspection apparatus of the second embodiment can also easily inspect the malfunction status of the image pickup unit in the endoscope, as in the first embodiment.

Third Embodiment

A third embodiment of the present invention will be described below.

Figure 8:
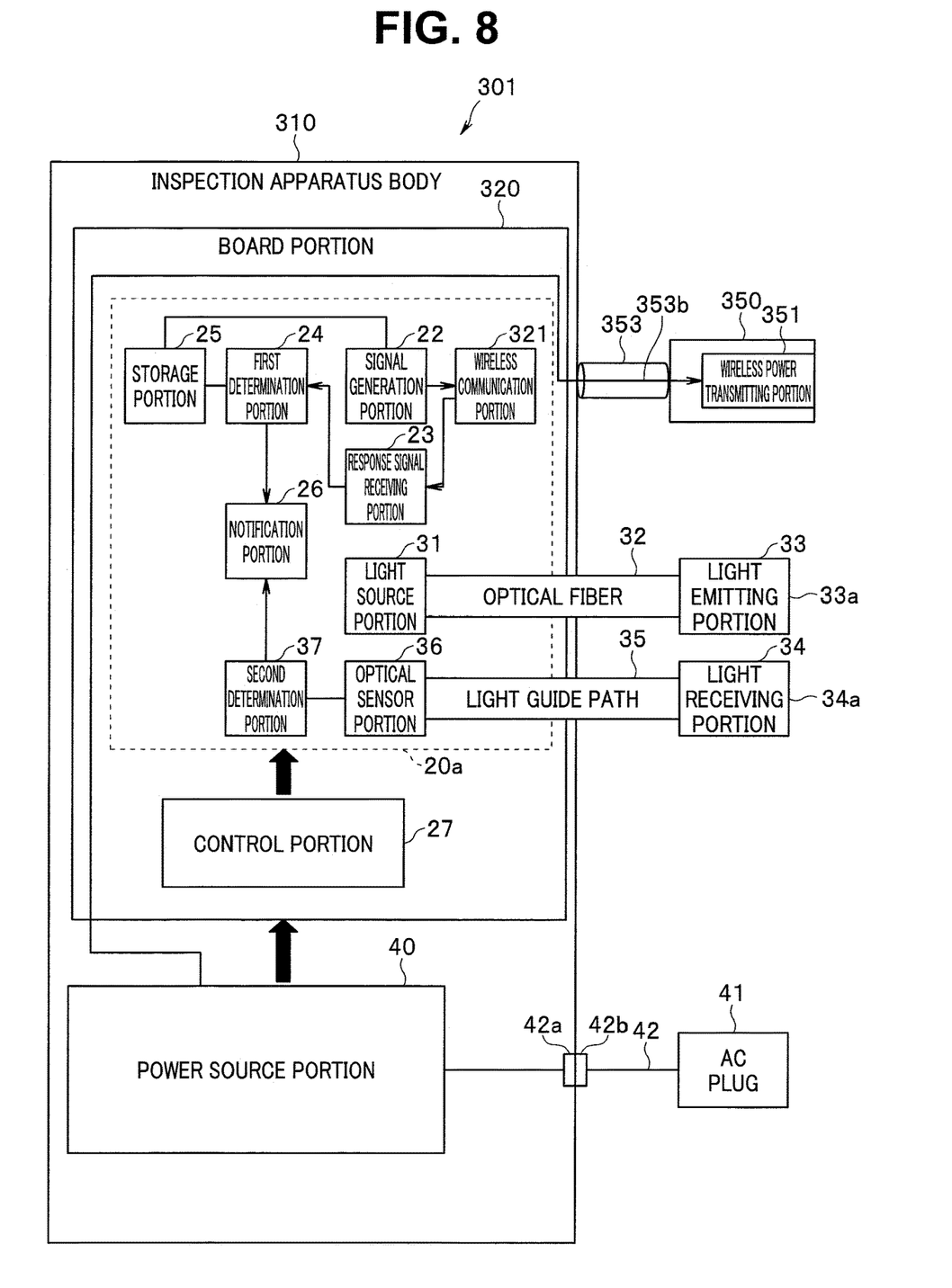
FIG. 8 is a block diagram showing an electrical configuration of an endoscope inspection apparatus of a third embodiment of the present invention.
Figure 9:
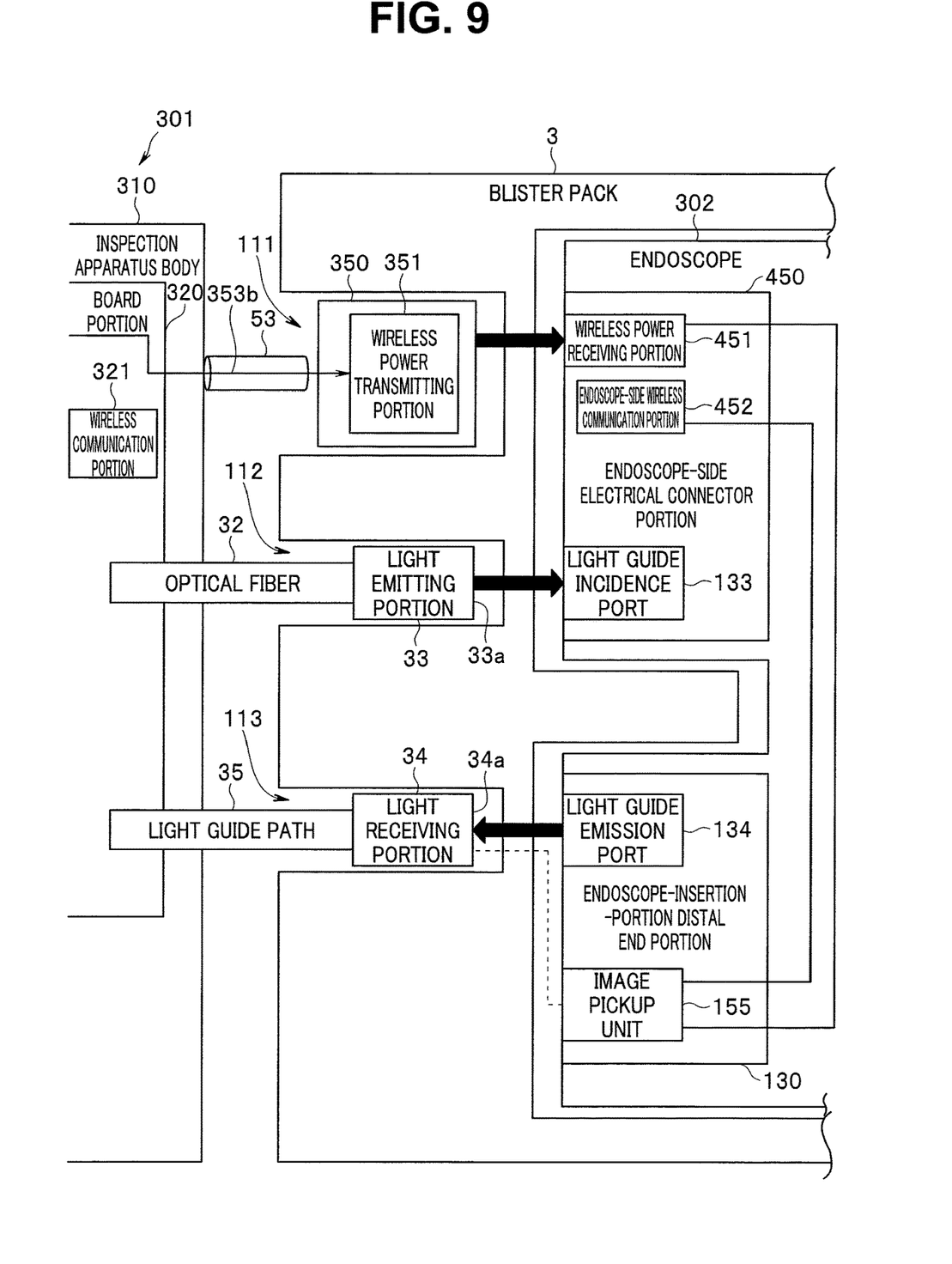
FIG. 9 is a block diagram showing an electrical connection state between the endoscope inspection apparatus of the third embodiment and an endoscope (to be inspected) packaged in a blister pack.

FIG. 8 is a block diagram showing an electrical configuration of an endoscope inspection apparatus of a third embodiment of the present invention, and FIG. 9 is a block diagram showing an electrical connection state between the endoscope inspection apparatus of the third embodiment and an endoscope (to be inspected) packaged in a blister pack An endoscope inspection apparatus 301 of the third embodiment is configured such that all of a drive signal transmitted from an inspection apparatus body toward the endoscope to be inspected and a response signal transmitted from the endoscope to the inspection apparatus body are transmitted and received in a wireless manner. Therefore, only the differences from the first embodiment will be described below, and the description of the common components will not be presented.

<Schematic Configuration of Endoscope 302>

First, a configuration of the endoscope 302 to be inspected by the endoscope inspection apparatus will be schematically described with reference to FIG. 9 before a description of the endoscope inspection apparatus of the third embodiment.

The endoscope 302 to be inspected by the endoscope inspection apparatus of the third embodiment has the same basic configuration as the configuration of the endoscope 2 according to the endoscope inspection apparatus of the first embodiment except that an endoscope-side electrical connector portion 450 includes a wireless power receiving portion 451 having a function similar to the function of the wireless power receiving portion 151 described above and an endoscope-side wireless communication portion 452 as a component portion instead of the endoscope-side communication connector 152 to transmit and receive a predetermined signal to/from a wireless communication portion 321 provided on the inspection apparatus body 310 in a wireless manner.

In other words, when the endoscope 302 is inspected, the endoscope-side wireless communication portion 452 serves as a receiving portion configured to receive a wireless signal from the wireless communication portion 321 in the inspection apparatus body 310 and also functions as a transmitting portion of the response signal indicating a status of the image pickup unit 155.

Other components are similar to the components of the first embodiment, and will not be described in detail.

<Configuration of Endoscope Inspection Apparatus of Third Embodiment>

The endoscope inspection apparatus of the third embodiment will be described below.

As described above, FIG. 8 is the block diagram showing the electrical configuration of the endoscope inspection apparatus of the third embodiment of the present invention, and FIG. 9 is the block diagram showing the electrical connection state between the endoscope inspection apparatus of the third embodiment and the endoscope (to be inspected) packaged in the blister pack.

As shown in FIGS. 8 and 9, the endoscope inspection apparatus 301 of the third embodiment includes an inspection apparatus body 310, an apparatus-side electrical connector portion 350 extending from the inspection apparatus body 310, an electrical cable 353, an optical fiber 32, a light emitting portion 33, a light receiving portion 34, a light guide path 35, and an AC plug 41 configured to supply a power source to the inspection apparatus body 310, for example.

Also in the third embodiment, the inspection apparatus body 310 is configured to receive the supply of a power source, which is a commercial power source, via the AC plug 41, but may be configured to receive the supply of a predetermined power source from a predetermined battery mounted on the inspection apparatus body 310.

As in the first embodiment, the inspection apparatus body 310 includes a board portion 320 on which various circuit portions related to the endoscope inspection are arranged and a power source portion 40 configured to generate a power source to be supplied to each of the circuits in the board portion 320 and the endoscope 302 to be inspected.

<Schematic Configuration of Board Portion 320 in Inspection Apparatus Body 310>

As shown in FIG. 8, for example, the board portion 320 includes function portions having respective functions, that is, mainly includes a wireless communication portion 321 capable of transmitting and receiving a predetermined signal to/from the endoscope 302 to be inspected, a signal generation portion 22 configured to generate a drive signal to be transmitted to the endoscope 302, a response signal receiving portion 23 capable of receiving a response signal from the endoscope 302, a first determination portion 24 configured to determine whether a status of the image pickup unit 155 in the endoscope 302 is good or poor, a storage portion 25 configured to store information related to the drive signal, and a notification portion 26 configured to notify predetermined information based on the result determined by the first determination portion 24.

As in the first embodiment, each of the function portions, for example, the first determination portion 24 mainly serves to inspect the image pickup unit 155 in the endoscope 302 to be inspected.

In addition, as in the first embodiment, the board portion 320 includes a light source portion 31 configured to generate inspection light to be supplied to the endoscope 302, an optical fiber 32 configured to transmit the inspection light, a light guide path 35 configured to transmit the inspection light sent from the endoscope 302, an optical sensor portion 36 configured to convert the inspection light into a predetermined electrical signal and output the electrical signal, and a second determination portion 37 configured to determine whether a status related to the light guide in the endoscope 302 is good or poor.

As in the first embodiment, each of the function portions, for example, the second determination portion 37 mainly serves to inspect the illumination optical system in the endoscope 302 to be inspected.

Further, the board portion 320 includes a control portion 27 configured to control the respective function portions (portions indicated by reference numeral 20a in FIG. 1) described above. The control portion 27 controls operations of respective circuits in the respective function portion 20a according to operation (not shown).

<Detailed Configuration of Board Portion 320>

As described above, the board portion 320 includes, as image-pickup-unit inspection function portions that inspect the image pickup unit 155 in the endoscope 302 to be inspected, the wireless communication portion 321, the signal generation portion 22, the response signal receiving portion 23, the first determination portion 24, the storage portion 25, and the notification portion 26.

The configurations of the storage portion 25 and the signal generation portion 22 are similar to the configurations in the first embodiment, but in the third embodiment, the drive signal generated by the signal generation portion 22 is transmitted to the endoscope 302 via the wireless communication portion 321 and the endoscope-side wireless communication portion 452 under the control of the control portion 27.

The wireless communication portion 321 is connected to the signal generation portion 22 and the response signal receiving portion 23, and has a function of transmitting the drive signal generated by the signal generation portion 22 to the endoscope-side wireless communication portion 452 in the endoscope 302 and receiving the response signal from the endoscope-side wireless communication portion 452, under the control of the control portion 27.

On the other hand, an electrical cable 353 is provided to extend from the inspection apparatus body 310, and a power source line 353*b* is internally provided.

In addition, the response signal receiving portion 23, the first determination portion 24, and the notification portion 26 have the same functions as the functions in the first embodiment.

<Configuration of Apparatus-Side Electrical Connector Portion 350>

As shown in FIGS. 8 and 9, the apparatus-side electrical connector portion 350 is disposed at a distal end portion of the electrical cable 353 extending from the inspection apparatus body 310, and is fitted into a first fitting portion 111 in the blister pack 3 configured to package the endoscope 302 to be inspected In addition, the apparatus-side electrical connector portion 350 is internally provided with a wireless power transmitting portion 351 configured to supply a power source to the endoscope 302. The wireless power transmitting portion 351 has the same configuration as the configuration of the wireless power transmitting portion 51 in the first embodiment, and thus will not be described in detail below.

As described above, the endoscope inspection apparatus of the third embodiment can also easily inspect the malfunction status of the image pickup unit in the endoscope, as in the first embodiment.

Note that the present invention is not limited to the above-described embodiments, and can be variously changed and modified without departing from the scope of the present invention.

What is claimed is:

1. An endoscope inspection system comprising:
    an endoscope inspection apparatus that inspects a status of an image pickup device circuit of an endoscope; and
    a package that encloses at least an endoscope connector of the endoscope, wherein
    the endoscope inspection apparatus comprises:
        a communication connector configured to transmit and receive a predetermined signal to and from the endoscope connector via the package; and
        a processor comprising hardware, the processor being configured to:
            generate a drive signal that is a signal transmitted via the communication connector and is used to drive the image pickup device circuit,
            receive a response signal from the image pickup device circuit configured to operate by the drive signal, the response signal being a signal received via the communication connector,
            determine, based on the received response signal, the status of the image pickup device circuit, and
            notify predetermined information based on a result of the determination of the status of the image pickup device circuit, and
    the package comprising:
        a first fixing shape portion that encloses at least the endoscope connector; and
        a first fitting shape portion fitted with the communication connector such that an endoscope-side communication terminal of the endoscope connector enclosed in the first fixing shape portion is electrically connected to an inspection apparatus-side communication terminal of the communication connector via the package.

2. The endoscope inspection system according to claim 1, wherein the processor generates the drive signal corresponding to a type of the endo scope.

3. The endoscope inspection system according to claim 2, further comprising:
    a memory configured to store information related to the drive signal corresponding to the type of the endoscope, wherein
    the processor generates the drive signal corresponding to the type of the connected endoscope, based on the information stored in the memory.

4. The endoscope inspection system according to claim 3, wherein
    the memory further stores pattern information of a reference response signal corresponding to the type of the endoscope, and
    the processor determines, based on the received response signal and the pattern information of the reference response signal stored in the memory, the status of the image pickup device circuit.

5. The endoscope inspection system according to claim 1, wherein the endoscope inspection apparatus further comprises:
    a light source configured to generate light to be supplied to the endoscope,
    a light emitting port configured to emit the light to an incidence port of a light guide of the endoscope,
    a light receiving component including a light receiving surface configured to receive the light guided by the light guide, the light being emitted from an emission port of the light guide provided at an insertion-portion distal end portion of the endoscope, and
    an optical sensor configured to convert the light received on the light receiving surface into a predetermined electrical signal and output the electrical signal, and
    the processor receives the electrical signal from the optical sensor, determines, based on the electrical signal, whether a status of the light guide of the endoscope, and notifies predetermined information based on a result of the determination of the status of the light guide of the endoscope.

6. The endoscope inspection system according to claim 5, wherein the package further encloses the insertion-portion distal end portion of the endoscope, the package further comprises a second fixing shape portion that encloses the packaged insertion-portion distal end portion and the light is received at the incidence port of the light guide of the endoscope and received at the light receiving component the via the package.

7. The endoscope inspection system according to claim 6, wherein
    the incidence port of the light guide is provided in the endoscope connector, and
    the package further includes a second fitting shape portion fitted with the light emitting component such that the light emitted from the light emitting component is incident on the incidence port in the endoscope connector enclosed in the first fixing shape portion.

8. The endoscope inspection system according to claim 7, wherein the package further includes a third fitting shape portion fitted with the light receiving component such that the light receiving surface is configured to receive the light emitted from the emission port of the light guide in the insertion-portion distal end portion enclosed in the second fixing shape portion.

9. An endoscope inspection apparatus that inspects a status of an image pickup device circuit of an endoscope in which at least an endoscope connector of the endoscope is enclosed in a package, the endoscope inspection apparatus comprising:
- a communication connector configured to transmit and receive a predetermined signal to and from the endoscope connector via the package, the communication connector being enclosed in a first fitting shape portion of the package;
- an inspection apparatus-side communication terminal provided in the communication connector and electrically connected to an endoscope-side communication terminal of an endoscope connector of the endoscope in a state where the communication connector is enclosed in the first fitting shape portion; and
- a processor comprising hardware, the processor being configured to
  - generate a drive signal that is a signal transmitted via the communication connector and is used to drive the image pickup device circuit,
  - receive a response signal from the image pickup device circuit configured to operate by the drive signal, the response signal being a signal received via the communication connector,
  - determine, based on the received response signal, the status of the image pickup device circuit, and
  - notify predetermined information based on a result of the determination of the status of the image pickup device circuit.

10. An endoscope package that packages a predetermined portion of an endoscope, wherein the package encloses at least an endoscope connector of the endoscope the package comprising:
- a first fixing shape portion that encloses at least the endoscope connector and
- a first fitting shape portion fitted with a communication connector such that an endoscope-side communication terminal of the endoscope connector fixed in the first fixing shape portion is electrically connected via the package to an inspection apparatus-side communication terminal of the communication connector of an endoscope inspection apparatus that inspects a status of an image pickup device circuit of the endoscope.

11. An endoscope inspection method of inspecting a status of an image pickup device circuit of an endoscope in which at least an endoscope connector of the endoscope is enclosed in a package, the method comprising:
- fitting a communication connector provided in an endoscope inspection apparatus and configured to transmit and receive a predetermined signal to and from the endoscope into a first fitting shape portion of the package;
- electrically connecting an inspection apparatus-side communication terminal of the communication connector via the package to an endoscope-side communication terminal of the endoscope connector of the endoscope in a state where the communication connector is enclosed in the first fitting shape portion;
- generating a drive signal that is a signal transmitted via the communication connector and is used to drive the image pickup device circuit;
- receiving a response signal from the image pickup device circuit configured to operate by the drive signal, the response signal being a signal received via the communication connector;
- determining, based on the received response signal, the status of the image pickup device circuit; and
- notifying predetermined information based on a result of the determination of the status of the image pickup device circuit.

* * * * *